(12) United States Patent
Bedell (10) Patent No.: US 9,913,963 B2
(45) Date of Patent: Mar. 13, 2018

(54) STEERABLE CATHETER WITH ELECTRICAL SIGNAL DELIVERED THROUGH STEERING WIRE

(71) Applicants: Advanced Pain Center, LLC, River Heights, UT (US); Shanna Bedell, River Heights, UT (US)

(72) Inventor: Raymond Bedell, Logan, UT (US)

(73) Assignee: ADVANCED PAIN CENTER, LLC., River Heights, UT (US)

( * ) Notice: Subject to any disclaimer, the term of this patent is extended or adjusted under 35 U.S.C. 154(b) by 0 days.

(21) Appl. No.: 15/410,208

(22) Filed: Jan. 19, 2017

(65) Prior Publication Data

US 2017/0128698 A1 May 11, 2017

Related U.S. Application Data

(63) Continuation of application No. 13/363,591, filed on Feb. 1, 2012, now Pat. No. 9,550,041.

(60) Provisional application No. 61/439,451, filed on Feb. 4, 2011.

(51) Int. Cl.
*A61M 25/01* (2006.01)
*A61B 18/14* (2006.01)
*A61M 25/10* (2013.01)
*A61N 1/36* (2006.01)
*A61N 7/00* (2006.01)

(52) U.S. Cl.
CPC ..... *A61M 25/0147* (2013.01); *A61B 18/1492* (2013.01); *A61M 25/0136* (2013.01); *A61M 25/10* (2013.01); *A61N 1/36017* (2013.01); *A61N 2007/0026* (2013.01)

(58) Field of Classification Search
CPC .......... A61M 25/0136; A61M 25/0144; A61M 25/0147; A61M 25/10; A61B 18/24; A61B 18/1492; A61N 1/0502; A61N 1/0551; A61N 1/36017; A61N 2007/0021
USPC ........ 600/434, 433; 607/117; 606/32, 34, 41
See application file for complete search history.

(56) References Cited

U.S. PATENT DOCUMENTS

| | | | | |
|---|---|---|---|---|
| 5,273,527 A | * | 12/1993 | Schatz | A61B 10/0291 604/164.13 |
| 5,383,852 A | * | 1/1995 | Stevens-Wright | A61M 25/0136 604/95.04 |
| 5,419,767 A | * | 5/1995 | Eggers | A61B 18/149 604/114 |
| 5,429,130 A | | 7/1995 | Goldman | |
| 5,873,842 A | | 2/1999 | Brennen et al. | |
| 6,030,360 A | | 2/2000 | Biggs | |
| 7,105,016 B2 | * | 9/2006 | Shiu | A61F 2/95 604/523 |
| 9,550,041 B2 | * | 1/2017 | Bedell | A61M 25/0136 |
| 2003/0004460 A1 | * | 1/2003 | Bedell | A61B 1/00082 604/95.04 |
| 2003/0045831 A1 | | 3/2003 | Ponzi et al. | |
| 2004/0116848 A1 | | 6/2004 | Gardeski et al. | |

* cited by examiner

*Primary Examiner* — Michael Carey
(74) *Attorney, Agent, or Firm* — Fabian VanCott; Steven L. Nichols

(57) ABSTRACT

A steerable catheter includes a body portion, a flexible catheter body with a proximal end and a distal tip and a continuous steering wire passing through the flexible body from the proximal end to the distal tip and turning back through the flexible body from the distal tip to the proximal end.

20 Claims, 9 Drawing Sheets

STEERABLE CATHETER WITH ELECTRICAL SIGNAL DELIVERED THROUGH STEERING WIRE

RELATED DOCUMENTS

The present application is a continuation of U.S. application Ser. No. 13/363,591, filed on Feb. 1, 2012, and issued as U.S. Pat. No. 9,550,041 B2. The present application claims priority from U.S. Provisional Application No. 61/439,451, entitled "Continuous Single Wire Steerable Catheter" filed Feb. 4, 2011, which applications are incorporated herein by reference in their entirety.

BACKGROUND

A catheter is a medical device that can be inserted into a body cavity, duct, or through a surgical opening. Catheters provide drainage, administration of fluids or gases, or access by surgical instruments. Steerable catheters allow for controlled deflection of the catheter. Steerable catheters provide a medical practitioner with increased control during insertion of the catheter and while administering medical treatment. Steerable catheters can be actuated in a number of ways, including using multiple steering wires. The multiple steering wires and their control devices can add a significant amount of cost, size, and complexity to the catheter system.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

A steerable catheter can be used in a variety of medical procedures to diagnose medical complaints, extract samples, provide drainage, administer fluids or gases, or provide access for surgical instruments. As discussed above, steerable catheters allow for controlled deflection of the catheter and provide increased control during insertion or retraction of the catheter. Steerable catheters can be actuated in a number of ways, including using multiple steering wires. The multiple steering wires and their control devices can add a significant amount of cost, size, complexity, and potential failure points to the catheter system.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

The illustrative systems, devices, and methods described below provide for a continuous single wire steered catheter that can be used in a diagnosis and treatment of a variety of medical complaints in the body including the epidural space. The illustrative catheter devices provide the ability to steer and deflect a distal portion of the catheter or sheath utilizing a continuous single steering wire. The steering wire is looped from a proximal portion of the catheter device through a distal end of a flexible body.

In one embodiment, a first end of the steering wire is anchored with respect to the flexible body and the second end of the steering wire can be both push and pull actuated. The actuation of the second end of the steering wire generates curvature and motion along the length of the flexible body. In an alternative embodiment, both the first and second ends of the steering wire are connected to an actuator wheel. As the actuator wheel is rotated, one end of the steering wire is pulled while the opposite end is pushed or relaxed. This provides motion of the flexible body in the desired direction.

As used in the specification and appended claims, the term "proximal" refers to a portion of an element or device that is nearer the operator of the device. The term "distal" refers to a portion of an element or device that is farther away from the operator of the device.

Figures 1A, 1B, 1C:
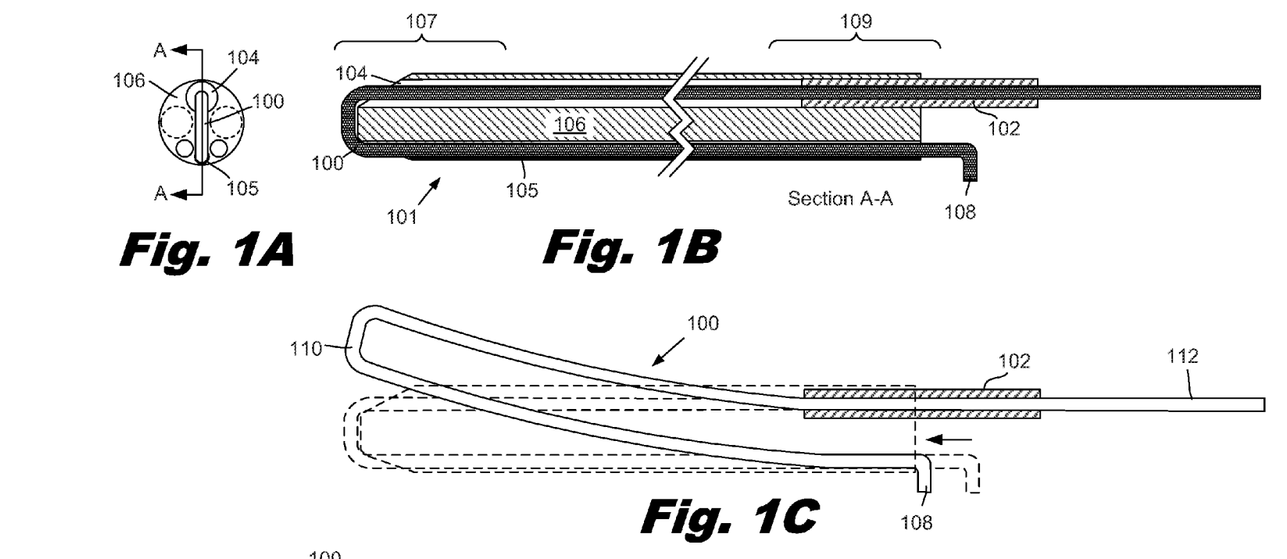
FIGS. 1A and 1B are an end view and a cross sectional view, respectively, of an illustrative continuous single wire catheter, according to one example of principles described herein.
FIGS. 1C and 1D are diagrams of bending of the illustrative continuous single wire produced by actuation of one end of the wire, according to one example of principles described herein.

FIGS. 1A and 1B are an end view and a cross sectional view, respectively, of an illustrative continuous single wire steerable catheter (101). The cross-sectional view shown in FIG. 1B is taken along line A-A in FIG. 1A. In this example, the continuous steering wire (100) passes through an anchor (102) in the proximal end (109) of a flexible body (106). According to one illustrative embodiment, the flexible body (106) is micro multi-lumen thin walled extruded tubing having a number of lumens running along its length. The combination of the wire (100) and the micro multi-lumen tube (106) provide enough stiffness for the catheter to adequately navigate in non-lumen tissues and yet are flexible enough to avoid damage to vascular and neurologic tissues.

The anchor (102) connects the portion of the wire (100) passing through it to the flexible body (106) so that this portion of the wire (100) does not move with respect to the flexible body (106). The wire (100) exits the anchor (102) and passes through a large lumen (104) in the flexible body (106) to the distal end (107) of the catheter (101). The wire exits the large lumen (104) and bends approximately 180° and reenters the flexible body (106) through a second smaller lumen (105). The wire passes through the second smaller lumen (105) and exits out of the proximal end (109) of the flexible body (106). In this example, the end of the steering wire (100) is bent to facilitate actuation. By moving the bent end (108) of the steering wire (100) toward or away from the flexible body (106), the catheter (101) can be bent with both a positive and negative curvature in a plane.

Figure 1D:
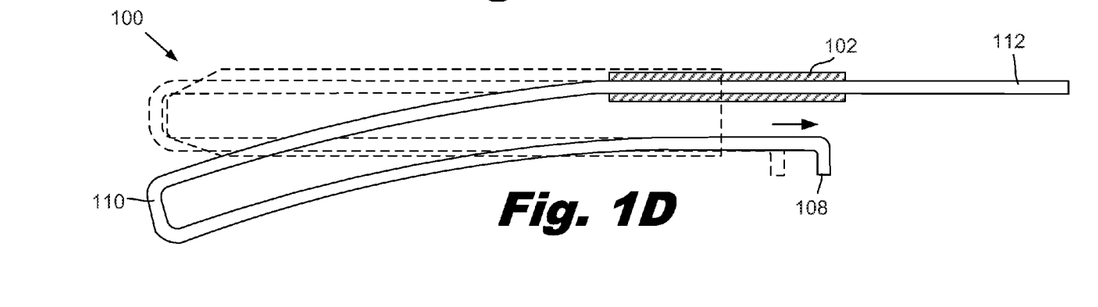

FIGS. 1C and 1D are diagrams of bending in the illustrative continuous single steering wire (100) produced by actuation of one end of the wire (100). For purposes of illustration, the deflected shape of the flexible body (106) is not shown in these figures. However, when the continuous single steering wire (100) moves in response to actuation, the flexible body (106) moves with the steering wire (100). The flexible body (106) also constrains the motion of the wire during bending to make the motion of the catheter (101) more repeatable.

In FIG. 1C, the bent end (108) of the wire is pushed toward the flexible body as shown by the arrow pointing to the left. This causes the steering wire (100) to deflect from its original at-rest position (shown by the dashed outline). This deflection causes a positive curvature in the wire and lifts the looped portion (110) of the wire (100). During the actuation of the wire (100), the anchor (102) holds the opposite stationary end (112) of the wire in place.

FIG. 1D is a diagram showing the actuated end (108) of the wire (100) being pulled away from flexible body (106) as shown by the arrow pointing to the right. This deflects the wire (100) from its original at-rest position (again shown by the dashed outline). The deflection causes a negative curvature in the wire (100) and lowers the looped portion (110) of the wire (100).

The single continuous steering wire (100) described above provides stiffness to the flexible member (106) and acts as a return spring that biases the motion of the catheter (101) to its at-rest position. Additionally, the steering wire (100) reduces the need for placing the deflection stress upon the walls of the flexible body (106) at the distal end. The steering wire (100) provides the stiffness of the shaft of the flexible body (106). Thus, the continuous single steering wire (100) pushes or pulls against itself and maintains its full integrity throughout repeated motions. This allows upward or downward deflection of the distal portion of the flexible member (106) up to 180 degrees in plane.

The steering wire (100) illustrated in FIGS. 1A-1D is shown as having a circular cross-section with a substantially uniform diameter over its length. However, a number of other geometries could be used. For example, a wire (100) with an oval or flattened cross section could be used. This alteration in the geometry of the wire (100) and lumens can be used to tailor the desired bending stiffness of the catheter (101). For example, an oval cross section wire has a lower bending stiffness in one direction than in the perpendicular direction. This can facilitate the controlled motion of the catheter (101) in one direction while providing increased rigidity in the perpendicular direction. The wire cross section or annealing could also change along the length of the steering wire (100) to tailor the stiffness of the catheter (101).

The steering wire (100) may be formed from any suitable resilient material. For example, the steering wire (100) may be formed from a biocompatible metal or metal alloy such as platinum, iridium, gold, titanium or alloys thereof. In one implementation, the steering wire (100) is formed from a stainless steel alloy or nickel-titanium alloy.

The actuator attached to the actuated end (108) of the wire (100) may be a thumb or finger slide mechanism, a wheel or rotating sleeve or any other suitable mechanism. Additionally, multiple wires may be passed in opposite directions with only one end of each continuous looped wire (100) attached to the actuator mechanism.

Figure 2:
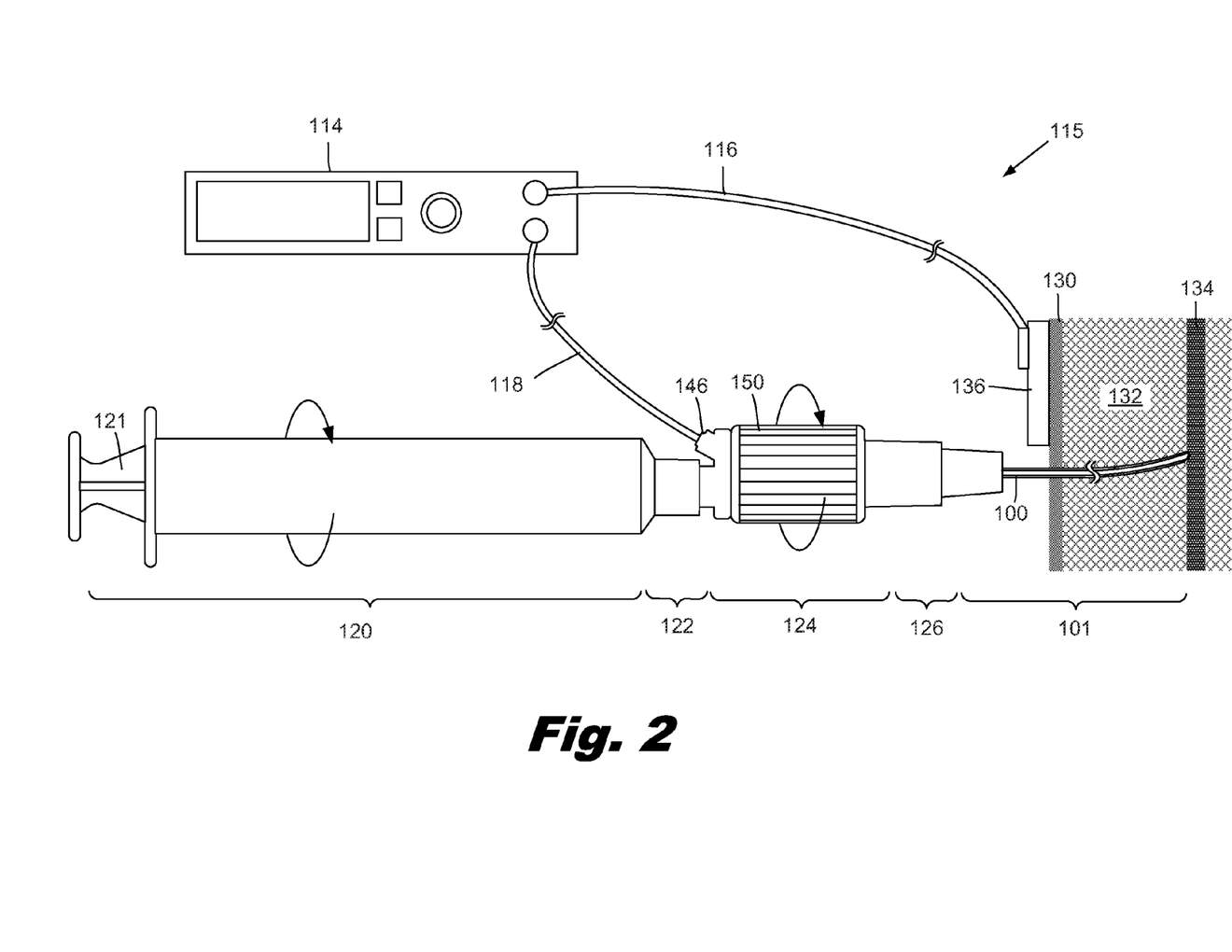
FIG. 2 is diagram of an illustrative continuous single wire steerable catheter system, according to one example of principles described herein.

FIG. 2 is a diagram of an illustrative continuous single wire steerable catheter system (115) being used in a medical procedure. The catheter system (115) includes a syringe (120), a catheter steering device (124), a catheter (101), and appropriate connecting devices (122, 126). In this example, the catheter steering device (124) is attached to the catheter (101) by a first luer lock (126) or other suitable connector. Manual rotation of a cylinder (150) on the catheter steering device (124) actuates a continuous single steering wire (100) in the catheter (101). By selectively rotating the cylinder (150), the catheter (101) can be shaped with the desired curvature.

In this example, the proximal end of the catheter steering device (124) is attached to a syringe (120) using a second luer lock (122). The syringe (120) may be a standard disposable syringe or a specialized syringe. The syringe (120) may hold a variety of pharmaceutical fluids or gasses that can be injected through the catheter steering device (124) and catheter (101) into the target tissues. The injection of the fluid or other injectate is accomplished by depressing the plunger (121) of the syringe (120).

The syringe (120) and catheter steering device (124) can be held in a single hand of the operator. The forefinger and thumb can be used to grasp and manipulate the cylinder (150) and the remaining fingers grasp and stabilize the syringe (120). In this example, depression of the syringe (120) can accomplished by repositioning the grasping hand or with a second hand. In other embodiments, the syringe (120) may be configured for electrically assisted or automatic actuation.

In some embodiments, other treatments may also be administered through the catheter (101) and catheter steering device (124). For example, an electrical stimulus maybe administered through the exposed tip of the continuous single steering wire (100). The electrical stimulus is generated by an electrical simulation unit (114) and passes through a stimulation wire (118) and into an auxiliary port (146) on the steering device (124). The stimulation wire (118) is connected in the steering device (124) to the steering wire (100). The tip of the steering wire (100) is maneuvered so that it comes into contact with the target tissue. An electrical current is then passed from the simulation unit (114) and into the steering wire (100). The electrical circuit is completed by placing a grounding pad (136) on the surface of the tissue (130). The grounding pad (136) is connected to the ground terminal of the stimulation unit (114) by the grounding wire (116).

This configuration could be used for a variety of applications. In one example, the continuous single wire steerable catheter system (115) is used to diagnose and treat compression of nerves in the spinal channel. A patient is first prepared and the grounding pad (136) is secured to the patient's skin (130). The catheter (101) is inserted through the skin (130) and overlying tissue (132) and brought into contact with a nerve (134) or other tissue. The catheter (101)

is controlled by a combination of manual manipulation of the entire catheter system (115) and rotation of the cylinder actuator (150). The manual manipulation of the entire catheter system (115) can include motions or combinations of motions in all six degrees of freedom. This can include linear motions in three directions and rotations around any of three orthogonal directions. For example, rotation of the entire catheter system is shown by the circular arrow around the syringe (120). This rotation angularly orients the steerable catheter (101) in the tissue (130, 132). As discussed above, manual rotation of the actuator cylinder (150) changes the curvature of the catheter (101). A combination of these motions allows a surgeon or other practitioner to appropriately contact the nerve (134). The continuous single wire steered catheter (110) and body tissues (130, 132, 134) can be visualized using a variety of methods, including fluoroscopy, fiber optics, video transmission, ultrasound, computed tomography, positron emission tomography, magnetic resonance imaging, nuclear resonance imaging, magnetic resonance tomography or other means to utilize real time or frozen images in a minimally invasive manner.

When the nerve or other selected tissue (134) is contacted, the electrical stimulation unit (114) can be actuated. The electrical stimulation therapy is delivered to the nerve (134) through the exposed tip of the steering wire (100). The patient can then use sensations caused by the electrical impulse to confirm that the stimulated nerve is or is not the nerve that is compressed or causing pain. If the stimulated nerve (134) is the target nerve causing pain, the syringe (120) can be actuated to dispense a pharmaceutical fluid through the catheter (101). For example, pain and/or anti-inflammatory medication could be administered or any other appropriate therapy. Following the treatment, the catheter is removed. In some embodiments, the entire catheter system (115) is disposable. In other embodiments, the catheter (101) and syringe (120) may be disposable while the catheter steering device (124) can be sterilized for reuse.

The continuous single wire steerable catheter system (115) can have a wide variety of other configurations depending on which medical procedure is being performed. For example, the auxiliary port (146) could be configured to accept a fiber optic cable for optical observation of tissues or application of laser energy. In some embodiments, the auxiliary port (146) could be used to supply radio frequency energy to the steering wire (100), ultrasound/laser diagnosis, or as an introductory port for another device.

Figure 3A:
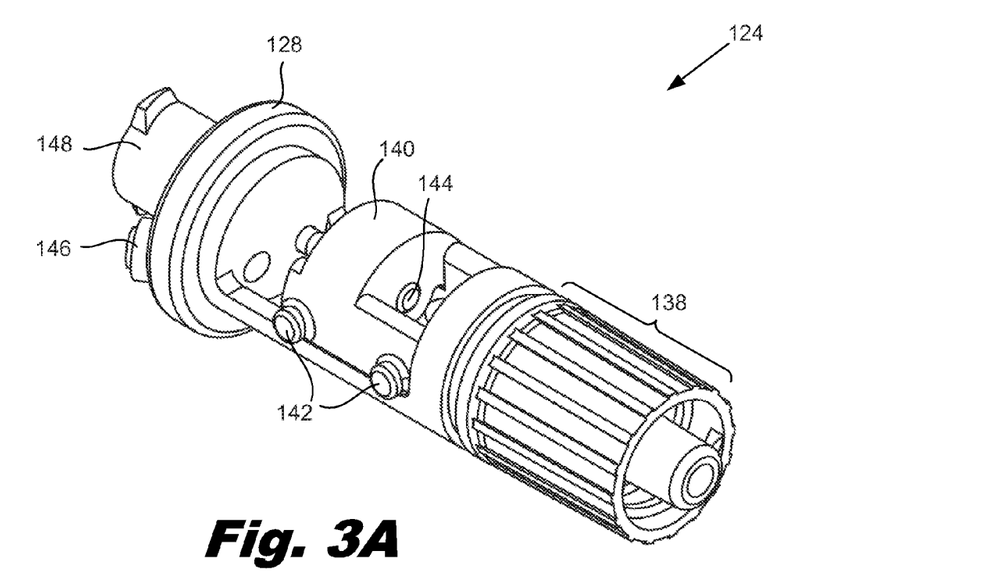
FIGS. 3A-3B are perspective views of a catheter steering device, according to one example of principles described herein.
Figure 3B:
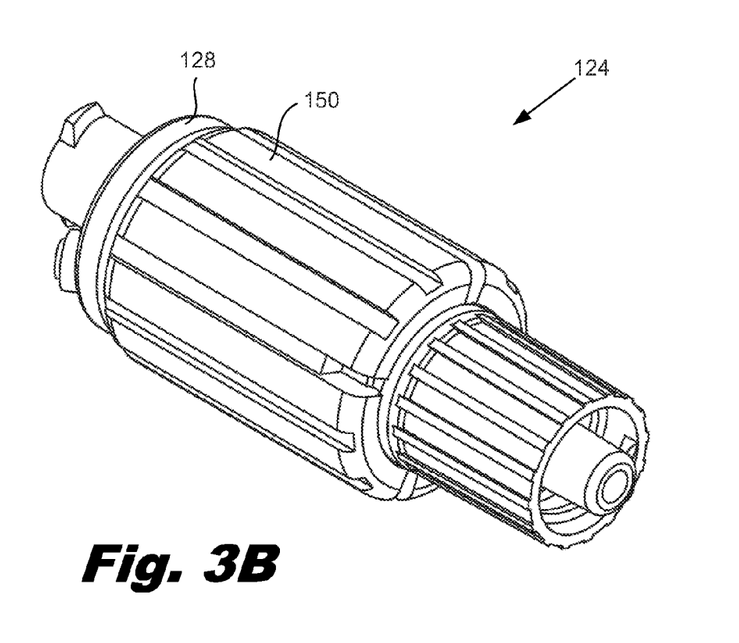
Figure 3C:
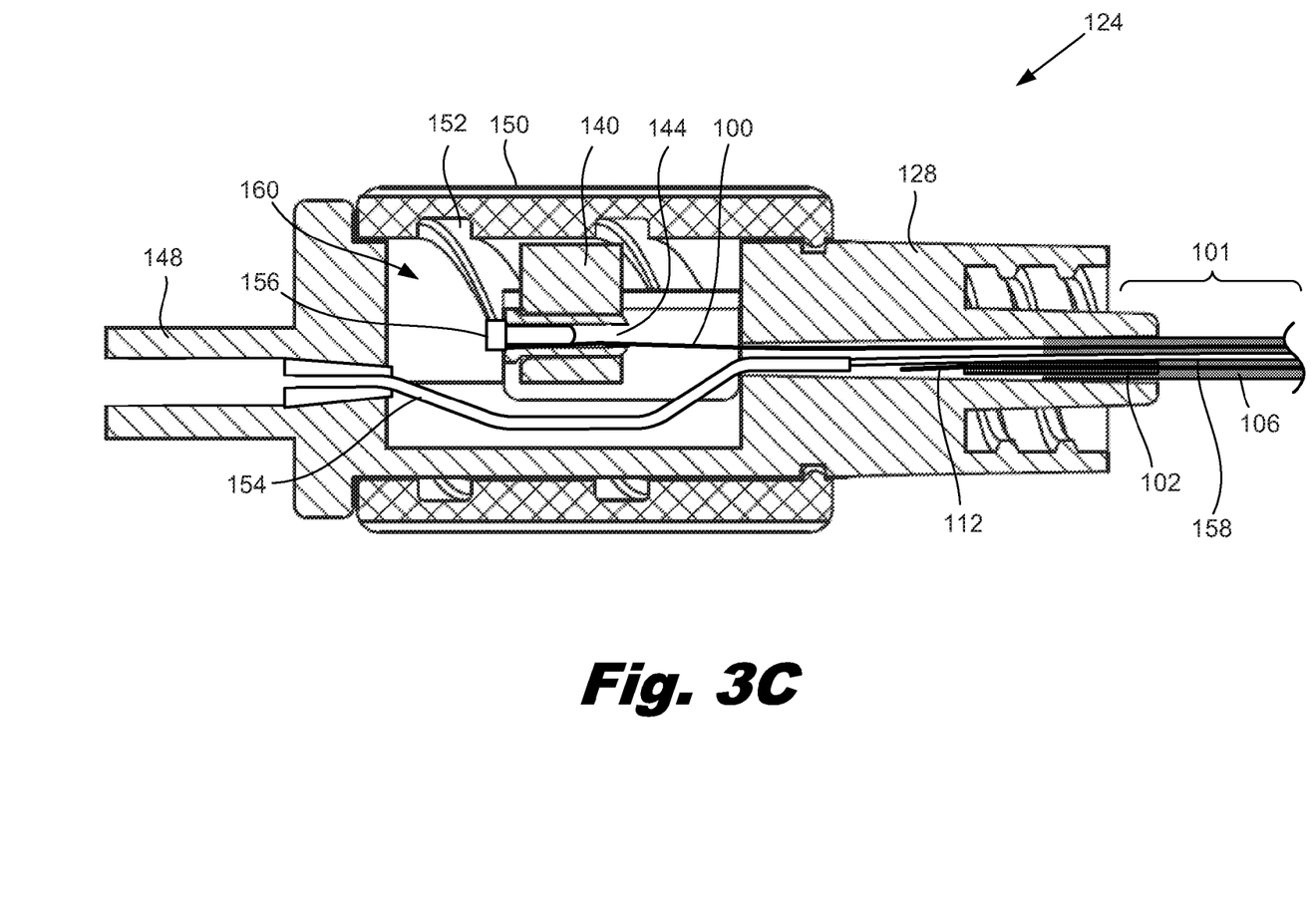
FIG. 3C is a cross-sectional view of a catheter steering device, according to one example of principles described herein.

FIGS. 3A-3C are diagrams that further illustrate one example of the catheter steering device (124). In this example, the catheter steering device (124) includes a body (128) and a slide (140). The body (128) includes a number of features including a female luer lock (138) on one end and a male luer lock (148) and the auxiliary port (146) on the opposite end. The slide (140) fits into a cutout in the center portion of the body (128). In this implementation, the slide (140) includes four knobs (142), two on each side. The slide (140) has a steering wire attachment aperture (144).

FIG. 3B shows the catheter steering device (124) with the cylinder (150) placed over the body (128) and slide (140, FIG. 3A). The knobs (142, FIG. 3A) fit into helical grooves in the interior of the cylinder (150) so that when the cylinder (150) is rotated around the body, the slide (140, FIG. 3A) slides along the cutout in the body (128).

FIG. 3C is a cross-sectional view of the catheter steering device (124) and attached catheter (101). The cross section is taken through the center of the device and bisects the slide (140) at the steering wire attachment aperture (144). As discussed above, the steering wire (100) has a fixed end (112) that is secured in place by the anchor (102). For example, the anchor (102) may be a segment of metal tubing that is secured to the wire (100) or a adhesive or epoxy that secures the wire to both the steering device body (128) and the flexible body (106). This prevents the motion of this portion of the steering wire (100). The fixed end (112) of the wire may extend beyond the anchor (102) and connect to the auxiliary port (146, FIG. 3A). The electrical stimulation can then be applied through the auxiliary port (146) to this end (112) of the wire (100).

As discussed above, the continuous single steering wire (100) passes through a lumen (104, FIG. 1B) in the flexible body (106) of the catheter (101) to its distal end (107, FIG. 1B) and then returns to the steering device (124) through a different lumen (105, FIG. 1B) in the flexible body (106). This actuated end (108, FIG. 1B, 1C) enters the steering wire attachment aperture (144) in the slide (140). A pin/epoxy (156) secures the actuated end (108, FIGS. 1B) in attachment aperture (144). As discussed above, the slide (140) has knobs (142, FIG. 3A) that fit into helical grooves (152) in the cylinder (150). As the cylinder (150) is rotated, the grooves (152) move the slide (140) forward and backward within the cavity (160).

The slide and cylinder mechanism described above is only one illustrative example of an actuator that could be used in conjunction with a continuous single wire steered catheter. A variety of other mechanisms could also be used.

The male luer lock (148) locks into the female luer lock receptacle on the syringe (120, FIG. 2). A tube (154) connects the male luer lock (148) to a fluid lumen (158) in the catheter (101). When the syringe (120, FIG. 2) is depressed, fluid passes through the tube (154) into the fluid lumen (158) and out of the tip of the catheter (101). Similarly, fluid samples may be drawn out of the tissue if desired by creating suction with the syringe (120, FIG. 2).

The illustrative configuration described above has a number of advantages, including low cost, small size, ease of assembly, and ease of use. Particularly, the attachment of the catheter (101) to the catheter steering device (124) involves relatively simple connections of one end of the steering wire (100) to the slide (140), the tube (154) to the fluid lumen (158) and an electrical connection between the auxiliary port (146, FIG. 3A) and the anchored end (112) of the steering wire (100). As discussed above, the entire catheter steering device (124) may be constructed as a disposable item. This eliminates the need to clean and sterilize the catheter steering device (124).

Figure 4A:
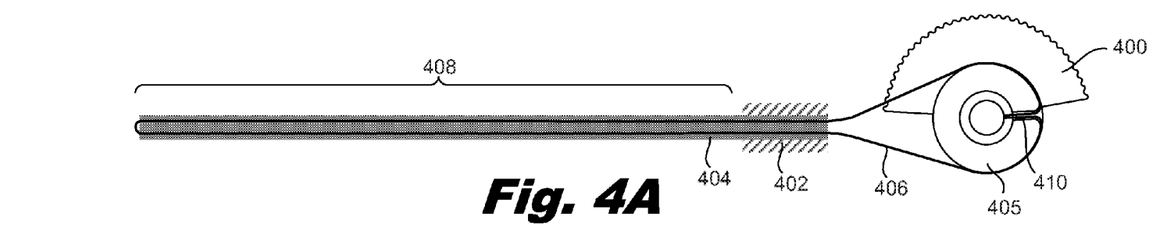
FIGS. 4A-4C are diagrams of an illustrative continuous single wire steerable catheter, according to one example of principles described herein.
Figure 4B:
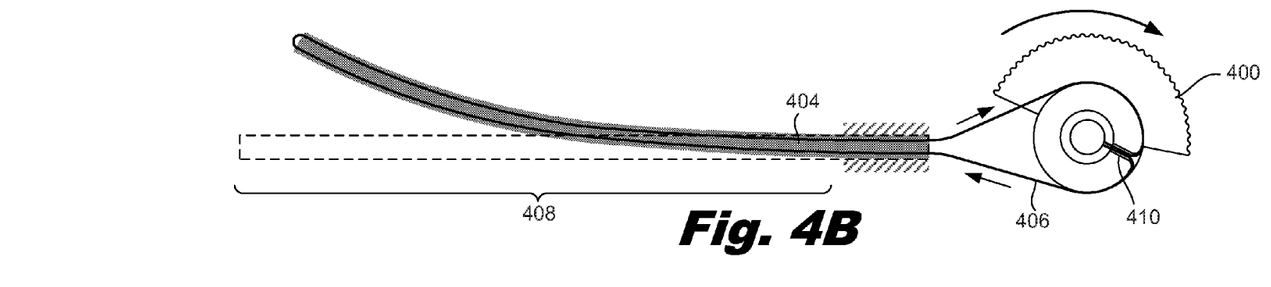
Figure 4C:
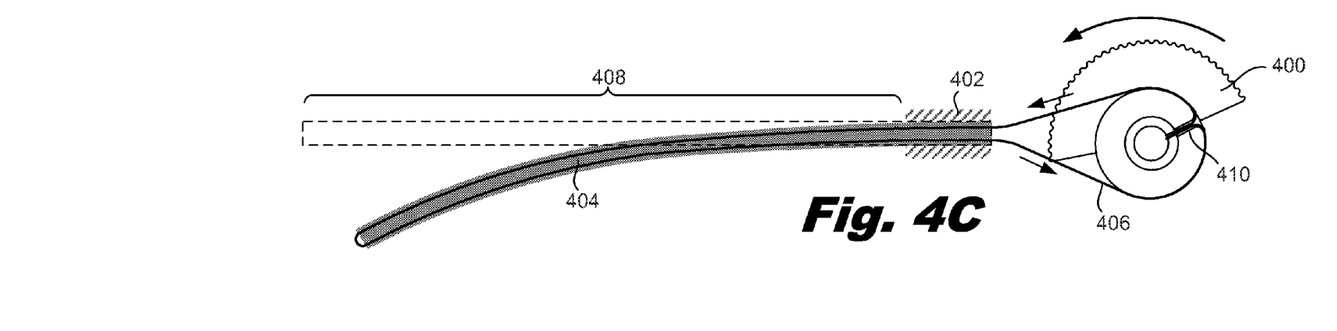

In addition to the illustrative example described above, a continuous single wire steerable catheter may have a number of other configurations. FIGS. 4A-4C are diagrams of an illustrative continuous single wire steerable catheter (408) that is actuated by rotating a wheel (400). FIG. 4A shows the catheter (408) in an at-rest or neutral position. The wheel (400) includes a toothed edge that is frictionally engaged by the operator's finger or thumb. The wheel (400) rotates around a central axis and has a cylinder (401) that has a slot (410) through its perimeter. The two ends of the wire (406) are secured into the slot (410), with the wire passing around the perimeter of the cylinder (401) and into the flexible body (404). The proximal end of the catheter (408) is attached to an anchor (402). The wire (406) then passes through an upper lumen in the flexible body (404) and then loops back through a lower lumen to the slot (410) in the cylinder (401).

FIG. 4B shows the actuation of the catheter by rotating the wheel (400) clockwise as shown by the curved arrow. This tightens the upper segment of the wire (406) and relaxes the lower segment of the wire (406). Linear arrows show the motion of the wire (406) when the wheel (400) is rotated. The catheter (408) arches upward and displaces the tip of the catheter. The at-rest position of the catheter (408) is shown by the dashed lines.

FIG. 4C shows the actuation of the catheter (408) with the opposite curvature by rotating the wheel (400) counter clockwise. The top segment of the wire (406) is relaxed and the bottom segment is tensioned. This causes the tip of the catheter (404) to drop.

Figures 5A, 5B:
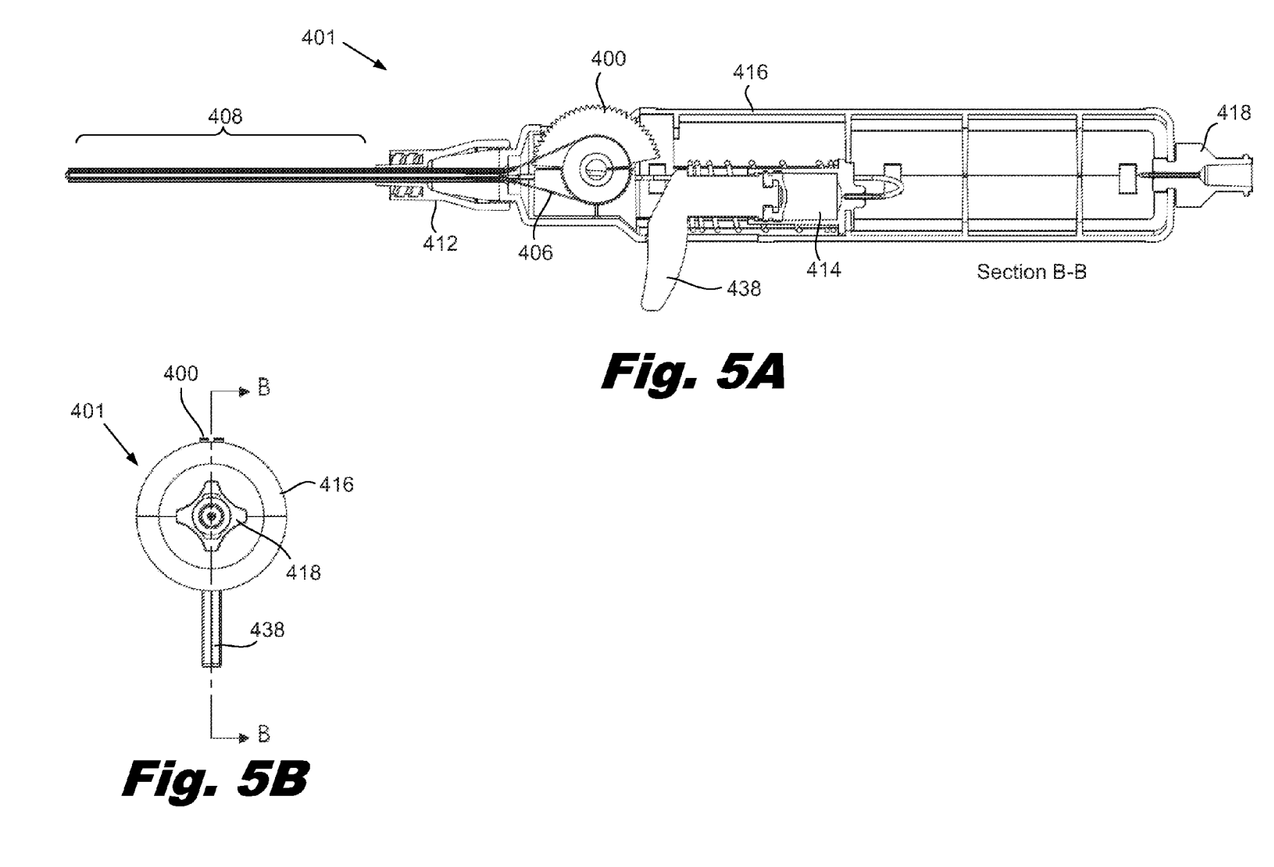
FIGS. 5A-5D are diagrams of an illustrative continuous single wire steerable catheter device, according to one example of principles described herein.

FIGS. 5A-5D are diagrams of an illustrative continuous single wire steerable catheter device (401). FIG. 5A is a cross sectional view taken along line B-B in FIG. 5B. This catheter device (401) includes a hollow handle portion (416) that supports and houses the actuation wheel (400) and a piston (414) with a trigger (438). On the proximal end of the handle portion (416) a male luer lock (418) is mounted. A fluid line can be attached to the male luer lock (418) to administer medication through the catheter (408). On the distal end of the handle portion (416) a female liter lock receptacle (412) supports the catheter (408). The handle portion (416) is designed so that the surgeon can easily and comfortably grasp the device (401).

The actuation wheel (400) extends up out of the handle portion (416) and the trigger (438) extends from the bottom of the handle portion (416). During use, the surgeon may grasp the handle portion (416) in one hand with their forefinger on the trigger (438) and their thumb on the wheel (400). This natural position allows depression of the trigger (438) and actuation of the wheel (400) to alter the curvature of the catheter (408) without shifting or loosening the surgeon's grip.

FIG. 5B shows a rear view of the continuous single wire steerable catheter device (401). This view shows the male luer lock (418), the handle portion (416) and the trigger (438). A small portion of the wheel (400) is visible at the top of the handle portion (416).

Figures 5C, 5D:
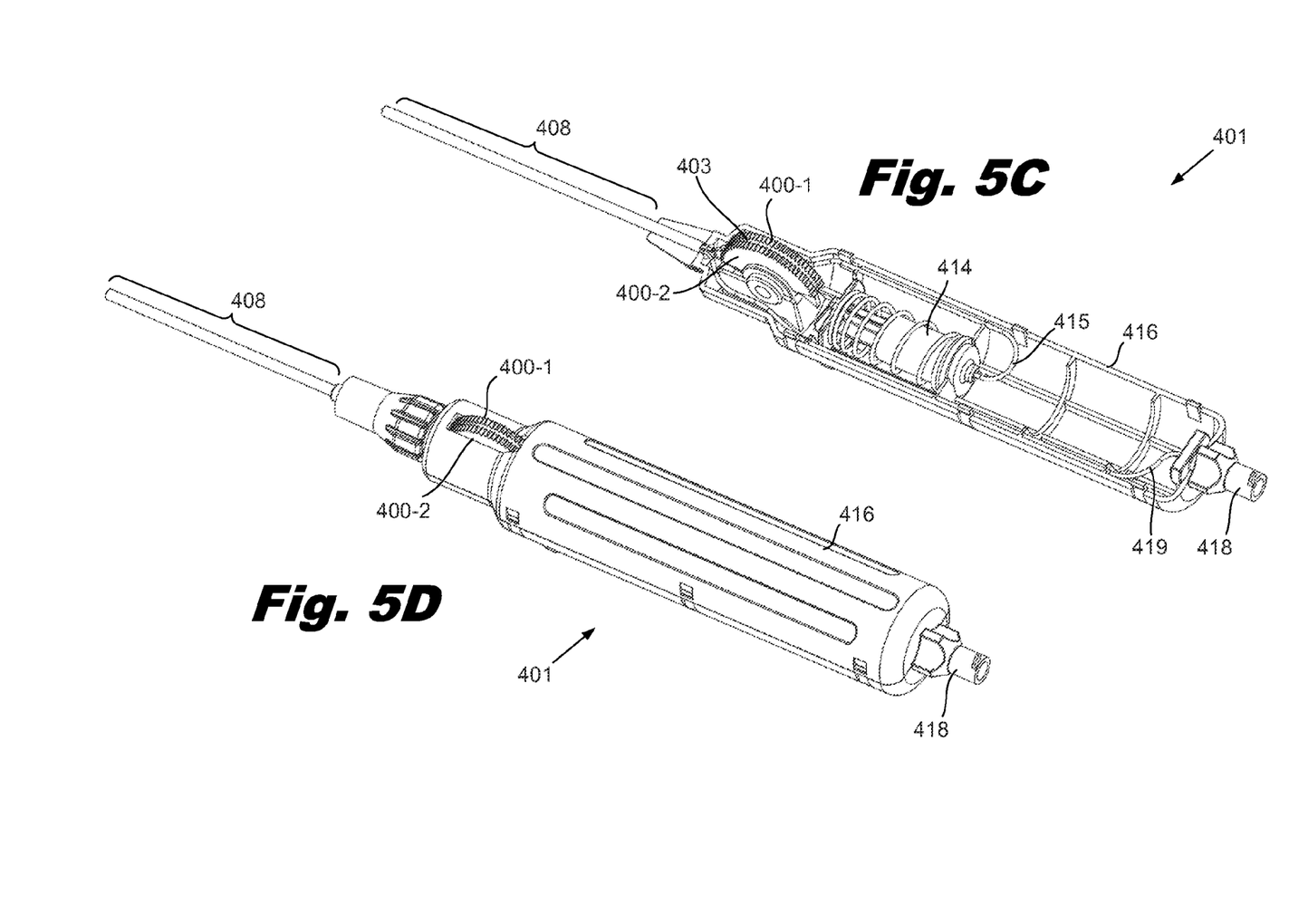

FIGS. 5C and 5D are perspective views of the continuous single wire steerable catheter device (401). In FIG. 5C, the upper shell of the handle portion (416) has been removed to expose the internal mechanisms of the catheter device (401). As discussed above, these mechanisms include a spring retractable piston (414), a male connector (418) with tubing (419) that fluidically connects the male connector (418) to a fluid lumen in the catheter (408) and the actuation wheel (400). in this embodiment, the wheel (400) includes two complimentary pieces (400-1, 400-2) that are joined together to form a central groove (403). The continuous single steering wire (406, FIGS. 4A-4C) is placed into this groove (403). The cylinder (405, FIG. 4A) forms the bottom of the groove (403). In one example, the assembly of the catheter (408) and actuation wheel (400) includes placing the ends of the steering wire around the cylinder (405, FIG. 4A) of a first piece (400-1) and into the slot (410, FIG. 4A-4C) in the cylinder. The second piece (400-2) is then joined to the first wheel piece (400-1) to create the groove (403) and lock the wires ends in the slot (410, FIGS. 4A-4C). FIG. 5D shows the upper shell of the catheter device (401) in place.

The illustrative catheter devices shown above have been engineered and developed to satisfy the needs of medical practitioners to more delicately and efficiently advance and direct catheters within body tissues. This allows for more rapid and precise diagnosis and treatment of their patients. The devices described above may be utilized in conjunction with any means of additional visualization including but not limited to fluoroscopy, magnetic resonant imaging, computed tomography scans, fiber optics, video camera, ultrasound or any other appropriate method for utilizing real time or frozen images in a minimally invasive manner.

Figure 6A:
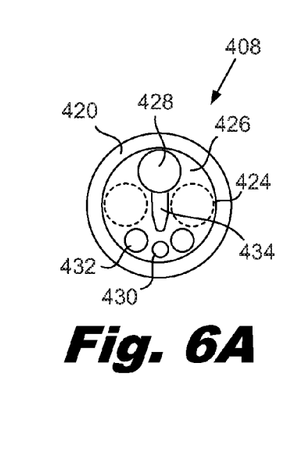
FIGS. 6A-6D are diagrams of an illustrative continuous single wire steerable catheter with an inflatable balloon near the tip, according to one example of principles described herein.
Figure 6B:
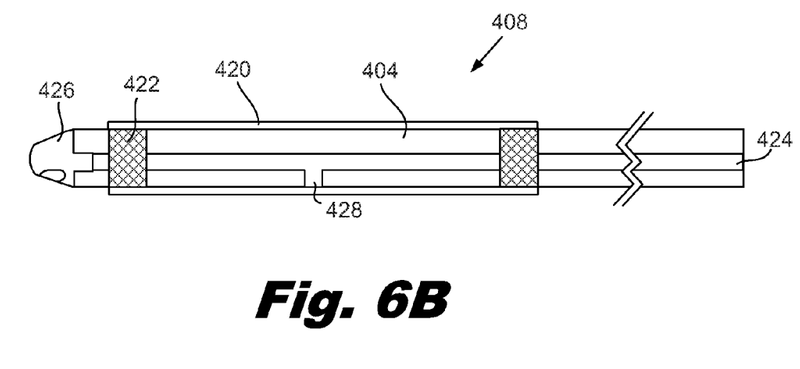
Figure 6C:
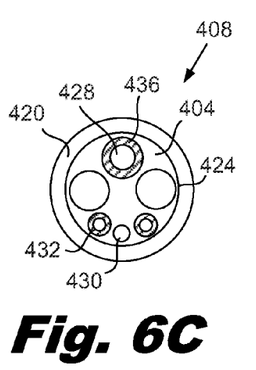

The spring retractable piston (414) can be actuated to displace fluid or gas out of the piston (414) and through tubing (415) that is connected to lumen in the catheter (408). According to one embodiment, this fluid or gas is used to inflate a balloon at or near the tip of the catheter (408). FIGS. 6A-6D are diagrams of an illustrative continuous single wire steerable catheter (408) with an balloon (420) at or near its distal tip. FIGS. 6A, 6B, and 6C are front, side, and rear views, respectively of the catheter with an uninflated balloon (420). FIGS. 6A and 6B show that the flexible body (404) in this example includes six lumens (428, 430, 432), four of which pass entirely through the catheter and two of which are plugged near the distal end by an end cap (426). In some embodiments, the cap (426) may be formed from optically clear polycarbonate so that imaging or other optical transmission can be performed. In other embodiments, the end cap (426) may be formed from another suitable material which is not optically clear, or may be absent.

The upper most lumen (428), the lowest lumen (430) and central indentation (434) accommodate the continuous single steering wire (406, FIG. 4A-4C). The other two through apertures (432) could be used for a variety of purposes, including the administration of liquid medication through the catheter (408). The two of the lumens (424) are plugged and could be used for a range of different purposes. In this example, at least one of the plugged lumens (424) is used to inflate the balloon (420) through a side vent (428).

FIG. 6B is a side view of the catheter (408) with an uninflated balloon (420). The balloon (420) may be formed from a variety of flexible materials including, but not limited to, YULEX. The balloon (420) is fastened to the flexible body (404) using adhesive (422). For example, the adhesive (422) may be cyanoacrylate that is dispensed around the perimeter of the flexible body in two different places. This adheres and seals the ends of a YULEX tube to the flexible body (404) so that it can be inflated.

FIG. 6C shows the proximal end of the catheter (408). On this end, all of the lumens (424, 428, 430, 432, 424) are open. Adaptors (436) are pushed into the end of some of the lumens. These adaptors may serve a variety of purposes. For example, where the catheter (408) is used in conjunction with a continuous single wire (100, FIGS. 1A-1C) like that illustrated in FIGS. 1A-1C, the adaptor (428) may serve as anchor that holds one end of the wire in place. Additionally, the adaptors may be portions of tubing that is inserted into the lumens to deliver fluid to the lumens (432).

Figure 6D:
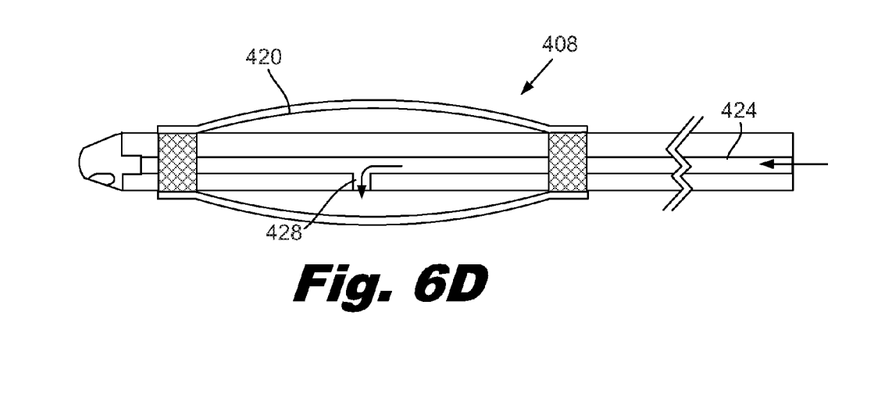

FIG. 6D shows the inflation of the balloon (420) by forcing air through a Distally plugged lumen, (or absent completely) (424) and out the side vent (428). The flow of air into the balloon (420) causes the balloon (420) to expand. This can be advantageously used to separate tissues, clear a fiber optic field of view, or temporarily secure the catheter (408) in place while medication is administered. The use of balloons in epidural tissues is further described in U.S. Pat. No. 7,273,468, to Raymond L. Bedell, titled "Steerable Fiberoptic Epidural Balloon Catheter and Scope" which is incorporated herein by reference in its entirety.

The embodiments described above are only illustrative examples. A variety of other configurations could be used. For example, the flexible tubing of the catheter is illustrated as having six lumens. However, depending on the design the flexible tubing could have 2, 3, 4, 5, or more lumens. Further, a wide variety of materials could be used to form the components. For example, the body of the catheters could be formed from PEBAX material. The hardness of the PEBAX material can be selected to provide the desired catheter stiffness. A relatively large catheter may be from PEBAX 3533 with a hardness of 35 using the appropriate Shore-Durometer test. Smaller catheters may use PEBAX or other materials with a greater hardness to achieve the desire amount of stiffness. The catheters described above may have a variety of geometries. In one embodiment, the length of the catheter (408) is about 300 millimeters and its diameter is approximately 1.6 to 2 millimeters, or could be as small as 1 mm or less.

Figure 7:
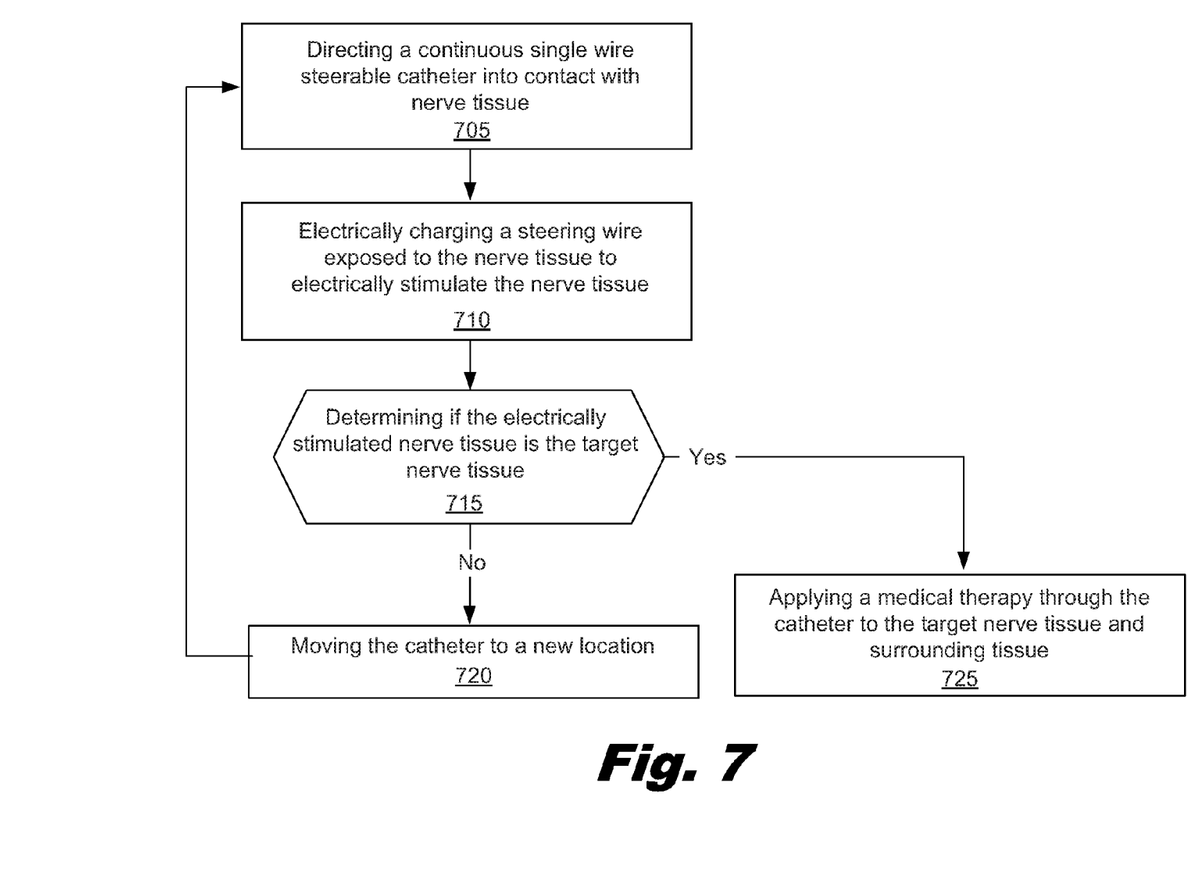
FIG. 7 is a flowchart of an illustrative method for using a continuous single wire steerable catheter device for diagnosis and treatment, according to one example of principles described herein.

FIG. 7 is a flow chart of a method for minimally invasive surgical procedures in spinal canal. The method includes directing a continuous single wire steerable catheter into contact with nerve tissue (block 705) and electrically charging a steering wire exposed to the nerve tissue to electrically stimulate or deliver other energy therapies to the nerve tissue (block 710). For example, the catheter can be directed into contact with nerve tissue by observing the position of the catheter using at least one of fluoroscopy, ultrasound, computed tomography, positron emission tomography, magnetic resonance imaging, nuclear resonance imaging, magnetic resonance tomography or other appropriate visualization technique.

This stimulation allows the patient or surgeon to determine if the electrically stimulated nerve tissue is the target nerve tissue (block 715). For example, the patient may have pain in their back and leg from a nerve that is pinched in their back. The electrical (stereotactic) stimulation of that nerve will cause a sensation in the patient's back and leg in the same areas where the pain occurs. This allows the patient to identify the nerve tissue as the target tissue. If the nerve tissue is not the target nerve tissue, moving the catheter to a new location (block 720) allows for alternative nerve tissue by repeating the process. This is shown by the arrow extending from block 720 to block 705. If the nerve tissue is the target nerve tissue, applying a medical therapy through the catheter to the target nerve tissue and surrounding tissue (block 725) can provide symptomatic relief to the patient. In some situations, the nerve tissue is located in the spinal canal and a balloon near the distal end of the catheter can be inflated to separate tissues in the spinal canal. The medical therapy can include applying a liquid drug through a lumen in the catheter, applying radio frequency energy through steering wire, applying laser energy through the catheter, applying ultrasound energy through the steering wire, or other appropriate therapy.

In sum, the continuous single wire steerable catheter has been designed to satisfy the needs of medical practitioners in more delicately and efficiently advancing and directing the flexible member of the catheter. This allows for more precise diagnosis and treatment of conditions and needs of their patients. Further, the simplicity of the device lowers the cost, size, and number of potential failure points in the device.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A steerable catheter comprising:
   a flexible body with a proximal end and a distal tip;
   a steering wire passing through the flexible body from the proximal end to the distal tip, the steering wire comprising an exposed portion at the distal tip of the flexible body, wherein the steering wire produces recoverable curving of the distal tip of the flexible body when force is applied on a proximal portion of the steering wire; and
   a port in a proximal portion of the catheter, the port in electrical communication with the exposed portion, such that when an electrical signal is provided to the port the electrical signal is available at the exposed portion of the steering wire.

2. The catheter of claim 1, in which the steering wire comprises a first end and a second end extending from the proximal end of the flexible body.

3. The catheter of claim 2, in which the first end of the steering wire is anchored to the flexible body and the second end of the steering wire is actuated to produce bending of the steering wire and flexible body.

4. The catheter of claim 3, in which actuation of the first end of the steering wire in a direction toward the flexible body moves the distal tip away from a neutral portion in a first direction.

5. The catheter of claim 4, in which actuation of the first end of the steering wire in a direction away from the flexible body moves the distal tip away from the neutral position in a second direction which is opposite the first direction.

6. The catheter of claim 5, in which the motion of the distal tip in the first direction and second direction is in a common plane.

7. The catheter of claim 2, further comprising a slide mechanism, the second end of the steering wire being attached to the slide mechanism.

8. The catheter of claim 7, further comprising a rotating cylinder placed over the slide mechanism such that helical grooves in the rotating cylinder engage with knobs on the slide mechanism and translate the slide mechanism when the cylinder is rotated.

9. The catheter of claim 2, in which the first end and second end of the steering wire are concurrently actuated in opposite directions to bend the flexible body.

10. The catheter of claim 9, further comprising a wheel, the first end and second end being secured to the wheel such that rotation of the wheel results in concurrent motion of the first end and second end in opposite directions.

11. The catheter of claim 1, further comprising an inflatable balloon.

12. The catheter of claim 11, in which the inflatable balloon is inflated by forcing a fluid through a lumen in the catheter using a piston or syringe.

13. The catheter of claim 1, in which the flexible body further comprises a medication lumen, medication being directed through the medication lumen and exiting at the distal tip of the flexible body.

14. The catheter of claim 1, further comprising a syringe connected to a lumen in the flexible body, the syringe being depressed to dispense fluid through the lumen to the distal tip of the flexible body.

15. The catheter of claim 1, in which the exposed portion of the steering wire at the distal tip of the flexible body is in electrical contact with surrounding biological tissues, and electrical stimulation being applied to the biological tissues through the steering wire.

16. The catheter of claim 1, in which the steering wire is a continuous steering wire passing through the flexible body from the proximal end to the distal tip and turning back through the flexible body from the distal tip to the proximal end.

17. The catheter of claim 1, in which the steering wire is fixed at the distal tip of the catheter.

18. The catheter of claim 1, in which the steering wire moves relative to the flexible body and the steering wire does not move relative to the distal tip of the flexible body.

19. The catheter of claim 1, in which only one steering wire extends from the proximal end of the flexible body to the distal tip of the flexible body.

20. A steerable catheter comprising:
- a flexible body with a proximal end and a distal tip;
- a single steering wire passing through the flexible body from the proximal end to the distal tip, the steering wire comprising an exposed portion at the distal tip of the flexible body, the steering wire fixed to the distal tip of the flexible body and able to move relative to the proximal portion of the flexible body in order to induce curvature in the distal tip of the flexible body; and
- a port in a proximal portion of the catheter, the port in electrical communication with a distal portion of the steering wire, such that when an electrical signal is provided to the port the electrical signal is available at the exposed portion of the steering wire at the distal tip of the flexible body.

\* \* \* \* \*